(12) United States Patent
Stewart et al.

(10) Patent No.: US 9,157,087 B2
(45) Date of Patent: Oct. 13, 2015

(54) INDUCIBLE PLANT PROMOTERS AND THE USE THEREOF

(71) Applicant: University of Tennessee Research Foundation, Knoxville, TN (US)

(72) Inventors: C. Neal Stewart, Knoxville, TN (US); Wusheng Liu, Knoxville, TN (US); Mitra Mazarei, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 296 days.

(21) Appl. No.: 13/794,255

(22) Filed: Mar. 11, 2013

(65) Prior Publication Data

US 2014/0007293 A1 Jan. 2, 2014

Related U.S. Application Data

(60) Provisional application No. 61/665,688, filed on Jun. 28, 2012.

(51) Int. Cl.
*C12N 15/82* (2006.01)

(52) U.S. Cl.
CPC ........ *C12N 15/8239* (2013.01); *C12N 15/8237* (2013.01); *C12N 15/8285* (2013.01)

(58) Field of Classification Search
None
See application file for complete search history.

(56) References Cited

U.S. PATENT DOCUMENTS 6,006,470 A * 12/1999 Geoghegan et al. ....... 47/58.1 R
8,088,976 B2 * 1/2012 Boukharov et al. ........... 800/285
2003/0101483 A1 * 5/2003 Hu et al. ....................... 800/279
2006/0272060 A1 * 11/2006 Heard et al. .................. 800/289
2007/0271630 A1 * 11/2007 Boukharov et al. .......... 800/279

FOREIGN PATENT DOCUMENTS

| EP | 2116606 A1 | 11/2009 |
|---|---|---|
| EP | 1718663 B1 | 7/2011 |
| EP | 2261227 B1 | 12/2011 |
| RU | 2406761 C2 | 12/2010 |

OTHER PUBLICATIONS

Doelling_Plant J_8_5_683-92_1995.*
Hao_J Biol Chem_273_26857-61_1998.*
Izawa_J Mol Biol_230_1131-44_1993.*
Maiti_Transgen Res_6_143-56_1997.*
Potenza_In Vitro Cell Dev Biol Plant_40_1_2004.*
International Search Report and Written Opinion dated Jun. 27, 2014 for co-pending European Patent Application No. 11830015.1, pp. 1-3.
Lilley et al., Effective Delivery of a Nematode-Repellent Peptide Using a Root-Cap Specific Promoter, Plant Biotechnol J., Feb. 2011, vol. 9, No. 2, pp. 151-161 (abstract only provided by Russian Patent Office).

* cited by examiner

*Primary Examiner* — Medina A Ibrahim
*Assistant Examiner* — Russell Boggs
(74) *Attorney, Agent, or Firm* — Johnson, Marcou & Isaacs, LLC; Ian J. Griswold (57) ABSTRACT

Disclosed are isolated nucleic acid molecules (inducible promoters) capable of directing expression in plant cell. In some embodiments, the promoters include a nucleic acid sequence set forth as SEQ ID NO: 1 or SEQ ID NO: 2, or a variant thereof. In some embodiments, the promoter is capable of gene expression in plants of an operably linked nucleic acid sequence. Disclosed are transgenic plants or parts thereof, that can include expression cassettes and/or expression vectors, which can be stably incorporated into the genome of the plant. Methods of regulating the expression of a polynucleotide of interest in a plant cell are also disclosed.

20 Claims, 2 Drawing Sheets

FIG. 2

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic promoter nucleic acid sequence

<400> SEQUENCE: 1
taaaataaag ttctttaatt                                               20

<210> SEQ ID NO 2
<211> LENGTH: 12
<212> TYPE: DNA
<213> ORGANISM: Artificial Sequence
<220> FEATURE:
<223> OTHER INFORMATION: Synthetic promoter nucleic acid sequence

<400> SEQUENCE: 2
atataattaa gt                                                       12
```

INDUCIBLE PLANT PROMOTERS AND THE USE THEREOF

CROSS-REFERENCE TO RELATED APPLICATION

This application claims the priority benefit of U.S. Provisional Application 61/665,688 filed on Jun. 28, 2012, which is incorporated by reference herein in its entirety.

STATEMENT OF GOVERNMENT SUPPORT

This invention was made with Government support under grant number 2010-342542-1139 awarded by the United States Department of Agriculture, National Institute of Food and Agriculture. The Government has certain rights in this invention.

FIELD OF THE DISCLOSURE

This disclosure is in the field of molecular biology. More specifically, this disclosure pertains to the field of genetic manipulation of plants, particularly the modulation of gene activity in plants, such as soybeans.

BACKGROUND

Genetic engineering of plants has enabled the production of plants having improved characteristics or traits, such as disease resistance, insect resistance, and herbicide resistance. New genes can be expressed in the plant cell to exhibit the desired phenotype such as a new trait or characteristic.

The proper regulatory signals, such as promoters, must be present and be in the proper location with respect to the coding sequence of a gene in order to obtain expression of a gene product inserted into a plant cell. For endogenous genes, a promoter is a DNA sequence that directs cellular machinery of a plant to produce RNA from the contiguous coding sequence downstream (3') of the promoter. The promoter region can influence the rate, developmental stage, and cell type in which the RNA transcript of the gene is made.

Expression of heterologous nucleotide sequences in a plant host depends in part upon the presence of an operably linked promoter that is functional within the plant host. The promoter sequence chosen is based on when and where within the organism expression of the heterologous nucleotide sequence is desired. Where expression in specific tissues or organs is desired, tissue-preferred promoters can be used. Where expression in response to a stimulus is desired, inducible promoters can be used. An inducible promoter is a promoter that is capable of directly or indirectly activating transcription of one or more DNA sequences or genes in response to an inducer. In the absence of an inducer, the DNA sequences or genes will not be transcribed, or will be transcribed at a level lower than in an induced state.

In the case of pest resistance, it is desirable to have a promoter that is induced by plant pests, including plant insect pests, nematodes or disease agents such as a bacterium, virus or fungus. For example, contact with a pathogen, or some other signal associated with the pathogen, induces activation of transcription, such that a pathogen-fighting protein or nucleic acid will be produced at a time when it will be effective in defending the plant. A pathogen-induced promoter may also be used to detect contact with a pathogen, for example by expression of a detectable marker, e.g., so that the need for application of pesticides can be assessed.

Soybean [*Glycine max* (L.) Merr.] is the most widely grown legume in the world, providing an important source of protein and oil. Soybean can be used in many ways such as ingredients in the formulation of a multitude of human foods, animal feed, and industrial products. As the dominant oilseed in world trade, soybean contributes to greater than about half of global oilseed production. Therefore, soybean is considered as one of the most important economic crops both in the U.S. and abroad. Although global soybean production has increased steadily, future demand for soybean still cannot be satisfied due to a growing world population and limited land resources.

During its entire life cycle, soybean may be attacked by many pathogens, such as fungi, bacteria, viruses, and nematodes, and suffer many diseases in any tissue. The soybean cyst nematode (*Heterodera glycines*, SCN) is the pest that causes the most economic damage of soybean in the U.S. SCN is a small plant-parasitic roundworm, and most stages of SCN cannot be seen by unaided eyes. SCN feeds on the soybean roots and robs nutrients from the soybean. When soybean plants are severely damaged by nematodes, they become stunted and turn chlorotic. Controlling SCN in commercial soybean productions remains difficult because SCN has a short life cycle and populations can build rapidly. Frequent changes in population virulence of SCN also contribute to the difficulty in the management of this pest. In addition, the cysts of SCN can survive in the soil for up to nine years and then break to release the eggs under proper conditions, increasing the probability of the nematodes' dispersing via infested soil.

The methods used to control and manage SCN in soybean production include crop rotation, the use of SCN-resistant cultivars, and the application of nematicides, which are often used in an integrated manner. However, these approaches often face economic restrictions, are time-consuming, and use of nematicides can result in environmental problems. Additionally, for some areas, economic factors may limit the use of crop rotation. Considering the long-term demands of soybean, it is critical to manage SCN infestation in soybean production. Thus, in implementing a transgenic approach to pest control, one strategy is to increase the expression of desirable nucleic acids and protein in response to pathogens. Consequently, there is a continued need for the controlled expression of nucleic acids and proteins deleterious to pests, for example in response to plant damage.

SUMMARY OF THE DISCLOSURE

Disclosed are isolated nucleic acid molecules (inducible promoters) capable of directing expression in a plant cell. In some embodiments, the promoters include a nucleic acid sequence set forth as SEQ ID NO: 1 or SEQ ID NO: 2, or a variant thereof. In some embodiments, the nucleic acid molecule includes one or more (such as two or more) of the nucleic acid sequences set forth as SEQ ID NO: 1 or SEQ ID NO: 2, or a combination thereof and variants thereof.

In some embodiments, the promoter capable of directing expression in plants is operably linked to a nucleic acid sequence of interest. In some embodiments, expression of the nucleic acid sequence of interest is induced by a pathogen elicitor treatment, a pathogen infection a condition associated with pathogen infection or infestation, or a combination thereof. In some examples, the pathogen is a nematode, such as a soybean cyst nematode. Also disclosed are expression cassettes that include the disclosed promoters operably linked to a nucleic acid of interest (for example a nucleic acid of interest that expresses a gene product of interest) such as a heterologous coding sequence, for example an insecticidal coding sequence, a nematicidal coding sequence, an antimicrobial coding sequence, an anti-fungal coding sequence, an anti-viral coding sequence, a visible marker coding sequence, a selectable marker coding sequence or any combination thereof. Such expression cassettes can be part of an expression vector, such as a plasmid. The nucleic acid of interest can encode a functional protein or RNA, for example an inhibitory RNA.

Also disclosed are transgenic plants or parts thereof, that can include the disclosed promoters, expression cassettes and/or expression vectors, which can be stably incorporated into the genome of the plant.

Methods of regulating the expression of a polynucleotide of interest in a plant cell are also disclosed. Such methods include, for example, stably incorporating in the genome of a plant or plant cell the polynucleotide sequence of interest operably linked to a disclosed promoter in the genome of the plant or plant cell and contacting the plant or plant cell with a substance or organism that induces the promoter.

BRIEF DESCRIPTION OF THE SEQUENCE LISTING

The nucleic and amino acid sequences shown herein are shown using standard letter abbreviations for nucleotide bases and amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named UTK_0146_ST25.txt, which was created on Mar. 1, 2013, is 1 kilobyte, and is incorporated by reference herein.

SEQ ID NOs: 1 and 2 are exemplary nucleic acid sequences of inducible promoters.

DETAILED DESCRIPTION

I. Introduction

Plant promoters have high value in plant biotechnology and agriculture, yet there is a dearth of characterized promoters that can be used in agricultural biotechnology applications. Promoters are key upstream DNA elements of genes that control gene regulation and it is desirable to tune them for specific expression patterns, yet this has rarely been accomplished.

Frequently it is desirable to modulate the level of expression of a nucleotide sequence of interest along with the temporal and spatial expression of the nucleotide sequence of interest in a plant. For example, increased resistance of a plant to infection by soil- and air-borne pathogens might be accomplished by genetic manipulation of the plant's genome to comprise an inducible promoter operably linked to the coding sequence of a heterologous herbicide-resistance gene or heterologous pathogen-resistance gene. Alternatively, it might be desirable to inhibit expression of a native DNA sequence within a plant's tissues to achieve a desired phenotype. In this case, such inhibition might be accomplished with transformation of the plant to comprise an inducible promoter operably linked to a coding sequence for an antisense RNA or other RNAi nucleotide sequence, such that expression of the sequence produces an RNA transcript that interferes with translation of the mRNA of the native DNA sequence.

Expression of heterologous DNA sequences in a plant host is dependent upon the presence of an operably linked promoter that is functional within the plant host. Choice of the promoter sequence will determine when and where within the organism the heterologous DNA sequence is expressed. Modifications of the promoter sequences or additional regulatory sequences upstream and/or downstream from the promoter sequence may be included in expression constructs to bring about varying levels of expression of heterologous nucleotide sequences of interest in a transgenic plant or plant cell.

Thus, isolation and characterization of promoter sequences that allow varying levels of expression, locations of expression, and inducible expression conditions of heterologous nucleotide sequences of interest in a transgenic plant or plant cell are needed for genetic manipulation of plants and plant cells. As disclosed herein, to meet the need for additional promoters for use in agricultural biotechnology applications, using bioinformatics analysis the inventors have designed novel inducible promoters, that have been shown to be inducible that are by the presence of nematodes, for example, the soybean cyst nematode (SCN), *Heterodera glycines*.

II. Summary of Terms

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710).

The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

To facilitate review of the various embodiments of this disclosure, the following explanations of terms are provided:

5' and/or 3': Nucleic acid molecules (such as, DNA and RNA) are said to have "5' ends" and "3' ends" because mononucleotides are reacted to make polynucleotides in a manner such that the 5' phosphate of one mononucleotide pentose ring is attached to the 3' oxygen of its neighbor in one direction via a phosphodiester linkage. Therefore, one end of a polynucleotide is referred to as the "5' end" when its 5' phosphate is not linked to the 3' oxygen of a mononucleotide pentose ring. The other end of a polynucleotide is referred to as the "3' end" when its 3' oxygen is not linked to a 5' phosphate of another mononucleotide pentose ring. Notwithstanding that a 5' phosphate of one mononucleotide pentose ring is attached to the 3' oxygen of its neighbor, an internal nucleic acid sequence also may be said to have 5' and 3' ends.

In either a linear or circular nucleic acid molecule, discrete internal elements are referred to as being "upstream" or 5' of the "downstream" or 3' elements. With regard to DNA, this terminology reflects that transcription proceeds in a 5' to 3' direction along a DNA strand. Promoter and enhancer elements, which direct transcription of the DNA sequence, are generally located 5' or upstream of the coding region. However, enhancer elements can exert their effect even when located 3' of the promoter element and the coding region. Transcription termination and polyadenylation signals are located 3' or downstream of the coding region.

Altering level of production or expression: Changing, either by increasing or decreasing, the level of production or expression of a nucleic acid molecule or an amino acid molecule (for example a gene, a polypeptide, a peptide), as compared to a control level of production or expression. In some examples, the production or expression is altered using one or more of the inducible promoters disclosed herein.

Agronomic trait: A characteristic of a plant, which includes, but is not limited to, plant morphology, physiology, growth and development, yield, nutritional enhancement, disease or pest resistance, or environmental or chemical tolerance. An "enhanced agronomic trait" refers to a measurable improvement in an agronomic trait including, but not limited to, yield increase, including increased yield under non-stress conditions and increased yield under environmental stress conditions, for example relative to a control plant. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits.

Amplification: When used in reference to a nucleic acid, this refers to techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744, 311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Cassette: A manipulable fragment of DNA carrying (and capable of expressing) one or more nucleic acid sequences of interest between one or more sets of restriction sites. A cassette can be transferred from one DNA sequence (usually on a vector) to another by "cutting" the fragment out using restriction enzymes and "pasting" it back into the new context. In disclosed embodiments, a cassette includes or more of the disclosed inducible promoters, preferably operable linked to a nucleic acid of interest, the expression of which is desired.

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells or other samples. In some examples cDNA is used as a source of a nucleic acid sequence of interest, such as a nucleic acid sequence of interest operable linked to a disclosed promoter.

Construct: Any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more transcribable polynucleotide molecule has been operably linked. In some examples a construct includes a nucleic acid sequence of interest operably linked to a disclosed promoter.

Control plant: A plant that does not contain a recombinant DNA that confers (for instance) an enhanced or altered agronomic trait in a transgenic plant, is used as a baseline for comparison, for instance in order to identify an enhanced or altered agronomic trait in the transgenic plant. As a non-limiting example, a suitable control plant may be a non-transgenic plant of the parental line used to generate a transgenic plant, or a plant that at least is non-transgenic for the particular trait under examination (that is, the control plant may have been engineered to contain other heterologous sequences or recombinant DNA molecules). Thus, a control plant may in some cases be a transgenic plant line that comprises an empty vector or marker gene, but does not contain the recombinant DNA, or does not contain all of the recombinant DNAs, in the test plant.

Disease resistance or pest resistance: The avoidance, reduction, delay and/or shortened duration of the harmful symptoms that are the outcome of the plant-pathogen interactions. Disease resistance and pest resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products.

As used herein, the term "pest" includes, but is not limited to, insects, fungi, bacteria, viruses, nematodes, mites, ticks, and the like. Insect pests include insects selected from the orders *Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera*. Viruses include but are not limited to tobacco or cucumber mosaic virus, ringspot virus, necrosis virus, maize dwarf mosaic virus, etc. Nematodes include but are not limited to parasitic nematodes such as root knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis, Globodera pallida* (potato cyst nematodes), *Rotylenchulus reniformis* (reniform nematode, a parasitic nematode on cotton), *Belonolaimus longicaudatus* (sting nematode). Lesion nematodes include but are not limited to *Pratylenchus* spp. Fungal pests include those that cause leaf, yellow, stripe and stem rusts.

DNA (deoxyribonucleic acid): DNA is a long chain polymer which comprises the genetic material of most organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule includes the reverse complement of that DNA molecule. Except where single-strandedness is required by the text herein, DNA molecules, though written to depict only a single strand, encompass both strands of a double-stranded DNA molecule.

Encode: A polynucleotide is said to encode a polypeptide if, in its native state or when manipulated by methods known to those skilled in the art, the polynucleotide molecule can be transcribed and/or translated to produce a mRNA for and/or the polypeptide or a fragment thereof. The anti-sense strand is the complement of such a nucleic acid, and the encoding sequence can be deduced therefrom.

Enhancer domain: A cis-acting transcriptional regulatory element (a.k.a. cis-element) that confers an aspect of the overall control of expression. An enhancer domain may function to bind transcription factors, which are trans-acting protein factors that regulate transcription. Some enhancer domains bind more than one transcription factor, and transcription factors may interact with different affinities with more than one enhancer domain. Enhancer domains can be identified by a number of techniques, including deletion analysis (deleting one or more nucleotides from the 5' end or internal to a promoter); DNA binding protein analysis using DNase I foot printing, methylation interference, electrophoresis mobility-shift assays, in vivo genomic foot printing by ligation-mediated PCR, and other conventional assays; or by DNA sequence comparison with known cis-element motifs using conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from promoters that include such elements, and they can be synthesized with additional flanking nucleotides that contain useful restriction enzyme sites to facilitate subsequence manipulation.

Expression: Transcription of a DNA molecule into a transcribed RNA molecule. More generally, expression encompasses the processes by which a DNA's coded information is converted into the structures present and operating in the cell. Expressed DNA sequences include those that are transcribed into mRNA and then translated into protein and those that are transcribed into RNA but not translated into protein (for example, siRNA, transfer RNA and ribosomal RNA). Thus, expression of a target sequence, such as a nucleic acid sequence of interest, can result in the expression of an mRNA, a protein, or both. The expression of the target sequence can be inhibited or enhanced (decreased or increased). Expression may be described as related to temporal, spatial, developmental, or morphological qualities as well as quantitative or qualitative indications.

Regulatory activity: The ability of a polynucleotide to affect transcription or translation of an operably linked transcribable polynucleotide molecule, such as an inducible promoter. An isolated polynucleotide molecule having regulatory activity, such as gene regulatory activity, may provide temporal or spatial expression or modulate levels and rates of expression of the operably linked transcribable polynucleotide molecule. An isolated polynucleotide molecule having regulatory activity may include a promoter (such as one or more of the promoters disclosed herein), intron, leader, or 3' transcription termination region.

Genetic material: A phrase meant to include all genes, nucleic acid, DNA and RNA.

Heterologous nucleotide sequence: A sequence that is not naturally occurring with a promoter sequence disclosed herein. While this nucleotide sequence is heterologous to the promoter sequence, it may be homologous, or native, or heterologous, or foreign, to the plant host. Additionally encompassed, is the expression of the homologous coding sequences of the promoters.

Increasing pest resistance or enhancing pest resistance: An enhanced or elevated resistance to a past over a normal or control plant or part thereof. In some examples, an increase or enhancement is an elevation of at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500% or more, for example relative to a control plant.

In cis: Indicates that two sequences are positioned on the same piece of RNA or DNA.

In trans: Indicates that two sequences are positioned on different pieces of RNA or DNA.

Insert DNA: Heterologous DNA within an expression cassettes, such as the disclosed expression cassette, used to transform the plant material while "flanking DNA" can comprise either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 20, 50, 100, 200, 300, 400, 1000, 1500, 2000, 2500, or 5000 base pair or greater which is located either immediately upstream of and contiguous with or immediately downstream of and contiguous with the original foreign insert DNA molecule.

Isolated: An "isolated" biological component (such as a nucleic acid, peptide or protein) has been substantially separated, produced apart from, or purified away from other biological components in the cell of the organism in which the component naturally occurs, e.g., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Operably linked: This term refers to a juxtaposition of components, particularly nucleotide sequences, such that the normal function of the components can be performed. Thus, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. A coding sequence that is "operably linked" to regulatory sequence(s), such as a disclosed promoter, refers to a configuration of nucleotide sequences wherein the coding sequence can be expressed under the regulatory control (e.g., transcriptional and/or translational control) of the regulatory sequences.

Plant: Any plant and progeny thereof. The term also includes parts of plants, including seed, cuttings, tubers, fruit, flowers, etc. As used herein, the term plant includes plant cells, plant organs, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, stalks, roots, root tips, anthers, and the like. Progeny, variants, and mutants of the regenerated plants are also included within the scope of the invention. The term plant cell, as used herein, refers to the structural and physiological unit of plants, consisting of a protoplast and the surrounding cell wall, including those with genetic alteration, such as transformation, has been affected as to a nucleic acid sequence of interest, or is a plant or plant cell which is descended from a plant or cell so altered and which comprises the alteration. A "control" or "control plant" or "control plant cell" provides a reference point for measuring changes in phenotype of the subject plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of a gene product of interest; or (e) the subject plant or plant cell itself, under conditions in which the gene product of interest is not expressed. The term plant organ, as used herein, refers to a distinct and visibly differentiated part of a plant, such as root, stem, leaf or embryo. More generally, the term plant tissue refers to any tissue of a plant in planta or in culture. This term includes a whole plant, plant cell, plant organ, protoplast, cell culture, or any group of plant cells organized into a structural and functional unit.

Polynucleotide molecule: Single- or double-stranded DNA or RNA of genomic or synthetic origin; that is, a polymer of deoxyribonucleotide or ribonucleotide bases, respectively, read from the 5' (upstream) end to the 3' (downstream) end.

Promoter: An array of nucleic acid control sequences which direct transcription of a nucleic acid. A plant promoter is a native or non-native promoter that is functional in plant cells. In one example, a promoter is a high level constitutive promoter, such as a tissue specific promoter. In another example, a promoter is an inducible promoter, such as one or more of the promoters disclosed herein.

Protoplast: An isolated plant cell without cell walls, having the potential for regeneration into cell culture or a whole plant.

Purified: The term purified does not require absolute purity; rather, it is intended as a relative term. Thus, for example, a purified protein preparation is one in which the protein is more enriched than the protein is in its generative environment, for instance within a cell or in a biochemical reaction chamber. Preferably, a preparation of protein is purified such that the protein represents at least 50% of the total protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. In some examples, a recombinant nucleic acid includes one or more of the promoters disclosed here, operatively connected to another nucleic acid sequence, such as a nucleic acid sequence encoding a gene product of interest.

Regulatable promoter or inducible promoter: A promoter the activity of which is regulated (directly or indirectly) by an agent, such as a transcription factor, a chemical compound, an environmental condition, or a nucleic acid molecule. In some examples, a regulatable promoter is one or more of the promoters disclosed herein, which haves been shown to be induced by a nematode (e.g., SCN) or conditions associated with a nematode, such as a nematode infestation.

Regulating expression: Processes of controlling the expression of a gene product by increasing or decreasing the expression, production, or activity of an agent that affects expression of the gene product. The agent can be a protein, such as a transcription factor, or a nucleic acid molecule, such as a miRNA or an siRNA molecule, which when in contact with the gene or its upstream regulatory sequences, or a mRNA encoded by the gene, either increases or decreases gene expression.

Regulatory sequences or elements: These terms refer generally to a class of polynucleotide molecules (such as DNA molecules, having DNA sequences) that influence or control transcription or translation of an operably linked transcribable polynucleotide molecule. Included in the term are promoters, enhancers, leaders, introns, locus control regions, boundary elements/insulators, silencers, Matrix attachment regions (also referred to as scaffold attachment regions), repressor, transcriptional terminators (a.k.a. transcription termination regions), origins of replication, centromeres, and meiotic recombination hotspots. Promoters are sequences of DNA near the 5' end of a gene that act as a binding site for RNA polymerase, and from which transcription is initiated. Enhancers are control elements that elevate the level of transcription from a promoter, usually independently of the enhancer's orientation or distance from the promoter. Locus control regions (LCRs) confer tissue-specific and temporally regulated expression to genes to which they are linked. LCRs function independently of their position in relation to the gene, but are copy-number dependent. It is believed that they function to open the nucleosome structure, so other factors can bind to the DNA. LCRs may also affect replication timing and origin usage. Insulators (also known as boundary elements) are DNA sequences that prevent the activation (or inactivation) of transcription of a gene, by blocking effects of surrounding chromatin. Silencers and repressors are control elements that suppress gene expression; they act on a gene independently of their orientation or distance from the gene. Matrix attachment regions (MARs), also known as scaffold attachment regions, are sequences within DNA that bind to the nuclear scaffold. They can affect transcription, possibly by separating chromosomes into regulatory domains. It is believed that MARs mediate higher-order, looped structures within chromosomes. Transcriptional terminators are regions within the gene vicinity that RNA polymerase is released from the template. Origins of replication are regions of the genome that, during DNA synthesis or replication phases of cell division, begin the replication process of DNA. Meiotic recombination hotspots are regions of the genome that recombine more frequently than the average during meiosis. Specific nucleotides within a regulatory region may serve multiple functions. For example, a specific nucleotide may be part of a promoter and participate in the binding of a transcriptional activator protein.

Isolated regulatory elements that function in cells (for instance, in plants or plant cells) are useful for modifying plant phenotypes, for instance through genetic engineering. In some examples, additional regulatory element are used in conjunction with a disclosed promoter.

RNA: A typically linear polymer of ribonucleic acid monomers, linked by phosphodiester bonds. Naturally occurring RNA molecules fall into three general classes, messenger (mRNA, which encodes proteins), ribosomal (rRNA, components of ribosomes), and transfer (tRNA, molecules responsible for transferring amino acid monomers to the ribosome during protein synthesis). Messenger RNA includes heteronuclear (hnRNA) and membrane-associated polysomal RNA (attached to the rough endoplasmic reticulum).

Screenable Marker: A marker that confers a trait identified through observation or testing.

Selectable Marker: A marker that confers a trait that one can select for by chemical means, e.g., through the use of a selective agent (e.g., an herbicide, antibiotic, or the like). Selectable markers include but are not limited to the expression products of antibiotic resistance genes, such as, kanamycin (nptII), G418, bleomycin, hygromycin, chloramphenicol, ampicillin, tetracycline, or the like. Additional selectable markers include a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulphonylurea resistance; or a methotrexate resistant DHFR gene. In one example, the selectable marker is AAD1.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Percent sequence identity is represented as the identity fraction multiplied by 100. The comparison of one or more polynucleotide or polypeptide sequences may be to a full-length polynucleotide or polypeptide sequence or a portion thereof, or to a longer polynucleotide sequence.

Methods of alignment of sequences for comparison are well known in the art. Various programs and alignment algorithms are described in: Smith and Waterman (Adv. Appl. Math. 2: 482, 1981); Needleman and Wunsch (J. Mol. Biol. 48: 443, 1970); Pearson and Lipman (PNAS. USA 85: 2444, 1988); Higgins and Sharp (Gene, 73: 237-244, 1988); Higgins and Sharp (CABIOS 5: 151-153, 1989); Corpet et al. (Nuc. Acids Res. 16: 10881-90, 1988); Huang et al. (Comp. Appls Biosci. 8: 155-65, 1992); and Pearson et al. (Methods in Molecular Biology 24: 307-31, 1994). Altschul et al. (Nature Genet., 6: 119-29, 1994) presents a detailed consideration of sequence alignment methods and homology calculations.

The alignment tools ALIGN (Myers and Miller, CABIOS 4:11-17, 1989) or LFASTA (Pearson and Lipman, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at with a web address of biology.ncsa.uiuc.edu.

Soybean: *Glycine max* and includes all plant varieties that can be bred with soybean.

Nematode resistance gene: A gene that, when expressed in a plant contributes to resistance to a nematode (e.g., SCN). Alternatively, a nematode resistance gene may be an allelic variant of the nematode resistance gene particularly variants resulting in a susceptible phenotype.

A transgenic event is produced by transformation of plant cells with a heterologous DNA construct(s), including a nucleic acid expression cassette that includes a transgene of interest, the regeneration of a population of plants resulting from the insertion of the transgene into the genome of the plant, and selection of a particular plant characterized by insertion into a particular genome location. In some embodiments of this disclosure, the transgene of interest is operably linked to a disclosed inducible promoter, such as SEQ ID NO: 1 or 2. An event is characterized phenotypically by the expression of the transgene(s). At the genetic level, an event is part of the genetic makeup of a plant. The term "event" also refers to progeny produced by vegetative propagation or a sexual outcross between the transformant and another variety that include the heterologous DNA. Even after repeated backcrossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

Transgenic plant: A plant that contains a foreign (heterologous) nucleotide sequence inserted into either its nuclear genome or organellar genome.

Transgene: A nucleic acid sequence that is inserted into a host cell or host cells by a transformation technique.

Transgenic: This term refers to a plant/fungus/cell/other entity or organism that contains recombinant genetic material not normally found in entities of this type/species (that is, heterologous genetic material) and which has been introduced into the entity in question (or into progenitors of the entity) by human manipulation. Thus, a plant that is grown from a plant cell into which recombinant DNA is introduced by transformation (a transformed plant cell) is a transgenic plant, as are all offspring of that plant that contain the introduced transgene (whether produced sexually or asexually). In some embodiments, a transgenic plant or cell can also contain an additional copy(ies) of a native plant sequence.

Transformation: Process by which exogenous DNA enters and changes a recipient cell. It may occur under natural conditions, or artificial conditions using various methods well known in the art. Transformation may rely on any known method for the insertion of foreign nucleic acid sequences into a prokaryotic or eukaryotic host cell. Selection of the method is influenced by the host cell being transformed and may include, but is not limited to, viral infection, electroporation, lipofection, and particle bombardment.

Vector: A nucleic acid molecule as introduced into a host cell, thereby producing a transformed host cell. A vector may include nucleic acid sequences that permit it to replicate in the host cell, such as an origin of replication. A vector may also include one or more coding sequences for therapeutic gene products and/or selectable markers and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which a disclosed invention pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); and Ausubel et al., Short Protocols in Molecular Biology: A Compendium of Methods from Current Protocols in Molecular Biology, 4th ed., Wiley & Sons, 1999.

III. Description of Several Embodiments

A. Inducible Promoters

Disclosed herein are promoters that were designed by the inventors that are inducible (for example, inducible by the presence of a nematode, such as the soybean cyst nematode (SCN), *Heterodera glycines* or a condition associated with nematode presence). As disclosed herein, these promoters can be induced as a consequence of plant pathogen infection (such as SCN infection), for example by pathogen elicitor treatment, pathogen infection, environmental conditions associated with pathogen infection or any combination thereof. In some embodiments, the promoter is an isolated nucleic acid molecule capable of directing expression in a plant cell, such as a cell of a monocot or dicot. The promoter sequences are useful for expressing operably linked nucleotide sequences (e.g., in an inducible manner), for example in a soybean plant, such as the root of a soybean plant. The sequences also find use in the construction of expression vectors for subsequent transformation into plants of interest, as probes for the isolation of other promoters, as molecular markers, and the like.

In specific embodiments, a disclosed promoter includes, such as consists essentially of or comprises, the nucleic acid sequence set forth as SEQ ID NO: 1 (TAAAATAAAGT-TCTTTAATT, motif 1.1) and/or SEQ ID NO: 2 (ATATAAT-TAAGT, motif 2.3) or a variant thereof. In specific examples, an inducible promoter is a nucleic acid molecule that includes a least one of the nucleic acid sequences set forth as SEQ ID NO: 1 or SEQ ID NO: 2 or a variant thereof. In specific examples, an inducible promoter is a nucleic acid molecule that includes at least two repeats, such as consecutive repeats, of the nucleic acid sequence set forth as SEQ ID NO: 1 and/or SEQ ID NO: 2 or a variant thereof, or a combination thereof. In representative embodiments, the promoter comprises at least 2, at least 3, at least 4, at least 5, at least 6, at least 7, at least 8, or at least 9, at least 10, at least 11, at least 12, at least 13, at least 14, at least 15, at least 16, at least 17, at least 18, or at least 19, at least 20, at least 30 or more of the repeats of the nucleic acid sequence set forth as SEQ ID NO: 1 or SEQ ID NO: 2 or a variant thereof, or a combination thereof, for example 2, 3, 4, 5, 6, 7, 8, 9, 10, 11, 12, 13, 14, 15, 16, 17, 18, 19, 20 or more repeats of the nucleic acid sequence set forth as SEQ ID NO: 1 or SEQ ID NO: 2, or a variant, or a combination thereof. In some examples, a promoter is between about 10 and about 5000 bases, and includes one or more copies of the nucleic acid sequence according to SEQ ID NO: 1 and/or 2 or a variant thereof, such as about 10, about 11, about 12, about 13, about 14, about 15, about 16, about 17, about 18, about 19, about 20, about 21, about 22, about 23, about 24, about 25, about 26, about 27, about 28, abut 29, about 30, about 35, about 40, about 45, about 50, about 75, about 100, about 125, about 150, about 175, about 200, about 250, about 300, about 350, about 400, about 450, about 500, about 750, about 1000, about 1500, about 2000, about 2500, about 3000, about 3500, about 4000 about 5000 or even greater, such as between about 10 and about 1000, about 20 and about 1500, about 50 and about 5000, about 10 and about 3000 and the like.

Variants of the disclosed promoter sequences are also contemplated by this disclosure. Variant nucleotide sequences also include synthetically derived nucleotide sequences, such as those generated, for example, by using site-directed mutagenesis, but which still exhibit promoter activity. Methods for mutagenesis and nucleotide sequence alterations are well known in the art. See, for example, Kunkel (1985) Proc. Natl. Acad. Sci. USA 52:488-492; Kunkel et al. (1987) Methods in Enzymol. 75:367-382; U.S. Pat. No. 4,873,192; Walker and Gaastra, eds. (1983) Techniques in Molecular Biology (MacMillan Publishing Company, New York) and the references cited therein. Generally, nucleotide sequence variants will have at least at least 40%, 50%, 60%, 65%, 70%, 75%, 80%, 85%, 90%, 91%, 92%, 93%, 94%, to 95%, 96%, 97%, 98%, 99% or more sequence identity to the disclosed promoters, such as determined by sequence alignment programs described elsewhere herein.

Biologically active variants (e.g., having promoter activity) are also encompassed by the embodiments. Biologically active variants include, for example, the native promoter sequences having one or more nucleotide substitutions, deletions, or insertions. Promoter activity may be measured by using techniques such as Northern blot analysis, reporter activity measurements taken from transcriptional fusions, and the like. See, for example, Sambrook et al. (1989) Molecular Cloning: A Laboratory Manual (2d ed., Cold Spring Harbor Laboratory Press, Cold Spring Harbor, N.Y.). Alternatively, levels of a reporter such as green fluorescent protein (GFP) or the like produced under the control of a promoter fragment or variant can be measured. See, for example, U.S. Pat. No. 6,072,050. Thus disclosed are promoters that have substantial sequence homology to SEQ ID NO: 1 or 2. Any functional or structural differences between substantially homologous sequences do not affect the ability of the sequence to function as a promoter. Two promoter nucleotide sequences are considered substantially homologous when they have at least about at least 40%, 50%, 60%, 65%, 70%, 75%, preferably at least about 80%, such as 81%, 82%, 83%, 84%, 85%, 86% 87%, 88%, 89%, more preferably at least about 90%, such as 91%, 92%, 93%, 94%, still more preferably at least about 95% sequence homology, such as at least 95% at least 96%, at least 97%, at least 98% at least 99% sequence identity or even greater.

In some embodiments, the disclosed promoters are altered to modulate the activity of the promoter. By "modulating" the transcriptional regulatory activity is intended to mean the transcriptional regulatory activity of the promoter sequence is either increased or decreased when compared to an appropriate control, for example when expression is induced. A decrease in transcriptional regulatory activity is intended to mean the transcription regulatory activity of the promoter is statistically lower than the activity of an appropriate control. An increase in transcriptional regulatory activity is intended to mean the transcription regulatory activity of the promoter is statistically higher than the activity of an appropriate control. In particular embodiments, modulating the transcriptional regulatory activity results in at least a 95% decrease or increase, at least a 90% decrease or increase, at least a 85% decrease or increase, at least a 80% decrease or increase, at least a 75% decrease or increase, at least a 70% decrease or increase, at least a 65% decrease or increase, at least a 60% decrease or increase, at least a 55% decrease or increase, at least a 50% decrease or increase, at least a 45% decrease or increase, at least a 40% decrease or increase, at least a 35% decrease or increase, at least a 30% decrease or increase, at least a 25% decrease or increase, at least a 20% decrease or increase, at least a 15% decrease or increase, at least a 10% decrease or increase, or at least a 5% decrease or increase of the transcriptional regulatory activity of the promoter or active variant or fragment thereof when compared to an appropriate control. Alternatively, modulating the transcriptional regulatory activity can include about a 0.5 fold, 1 fold, 2 fold, 4 fold, 8 fold, 16 fold, or 32 fold overall decrease or increase of the transcriptional regulatory activity of the promoter or active variant or fragment thereof when compared to an appropriate control. In other embodiments, modulating the transcriptional regulatory activity of a promoter or active variant or fragment thereof results in a decrease or an increase in the transcription regulatory activity of about 2%-15%, 10%-25%, 20%-35%, 30%-45%, 40%-55%, 50%-65%, 60%-75%, 70%-90%, 70% to 80%, 70%-85%, 80%-95%, 90%-100% when compared to an appropriate control. It is further recognized that the modulation of the transcriptional regulatory activity need not be an overall increase or decrease in activity but also includes a change in tissue distribution of the regulatory activity, a modification of the location within a cell of the gene product the expression of which is regulated by the promoter, or an alteration in response to specific inducing factors. If multiple transcripts are produced from a single polynucleotide sequence, modulation of the transcriptional regulatory activity could alter the native ratio of transcripts to increase one in relation to the other transcript or other transcripts.

Modifications of the disclosed promoter sequences can provide for a range of expression. Thus, they may be modified to be weak promoters or strong promoters. Generally, a "weak promoter" is a promoter that drives expression of a coding sequence at a low level, for example at levels of about 1/10,000 transcripts to about 1/100,000 transcripts to about 1/500,000 transcripts. Conversely, a strong promoter drives expression of a coding sequence at a high level, for example at about 1/10 transcripts to about 1/100 transcripts to about 1/1,000 transcripts.

The disclosed promoter sequences, when operably linked to a heterologous nucleotide sequence of interest and inserted into a transformation expression cassettes and/or expression vector according to methods known in the art, inducibly drive expression of the heterologous nucleotide sequence in the cells of a plant stably transformed, that is in a regulated manner. It is recognized that to increase transcription levels, enhancers or other regulatory elements may be utilized in combination with the disclosed promoters.

Enhancers are nucleotide sequences that act to increase the expression of a promoter region. Enhancers are known in the art and include the SV40 enhancer region, the 35 S enhancer element, and the like. An example of a regulatory element that provides for the recognition for RNA polymerase or other transcriptional factors to ensure initiation at a particular site is a promoter element. It is to be understood that nucleotide sequences, located within introns, or 3' of the coding region sequence may also contribute to the regulation of expression of a coding region of interest. Examples of suitable introns include, but are not limited to, the maize IVS6 intron, or potato LS1 INTRON2 (Vancanneyt, G., et al., (1990) Mol Gen Genet., 220, 245-250). A regulatory element may also include those elements located downstream (3') to the site of transcription initiation, or within transcribed regions, or both. In the context of the present disclosure, a post-transcriptional regulatory element may include elements that are active following transcription initiation, for example translational and transcriptional enhancers, translational and transcriptional repressors, and mRNA stability determinants.

The enhancers and other regulatory elements, or fragments thereof may be operatively associated with the disclosed promoters in order to modulate the activity of the promoter. Such modulation includes enhancing or repressing transcriptional activity, modulating post-transcriptional events, or both enhancing or repressing transcriptional activity and modulating post-transcriptional events.

In some embodiments, a disclosed inducible promoter capable of directing expression in plants is operably linked to a heterologous nucleic acid sequence and expression of the heterologous nucleic acid sequence is induced by a pathogen elicitor treatment, a pathogen infection, an environmental condition associated with pathogen infection or any combination thereof. In specific embodiments, the pathogen is a nematode, such as a soybean cyst nematode.

B. Expression Cassettes

The nucleotide sequences for the disclosed promoters are useful in the genetic manipulation of any plant when operably linked with a heterologous nucleotide sequence whose expression is to be controlled to achieve a desired phenotypic response. By "operably linked" is intended the transcription or translation of the heterologous nucleotide sequence is under the influence of the promoter sequence. In this manner, the nucleotide sequences for the promoters of this disclosure are provided in expression cassettes along with nucleotide sequences of interest for expression in the plant of interest. Such expression cassettes will typically comprise a transcriptional initiation region including one of the disclosed promoter nucleotide sequences, or variants thereof, operably linked to the heterologous nucleotide sequence whose expression is to be controlled by the promoters. Such an expression cassette can be provided with a plurality of restriction sites for insertion of the nucleotide sequence to be under the transcriptional regulation of the promoter and optionally additional regulatory sequences. The expression cassette may additionally contain selectable markers or sequences.

The disclosed promoters, such as one or more of SEQ ID NOs: 1 and/or 2 or variants thereof, for example between 2 and 10 repeats of SEQ ID NOs: 1 and/or 2 can be part of an expression cassette, such as an expression cassette that includes one or more of the disclosed promoters operably liked to a heterologous coding sequence. In some examples, the expression cassette includes a heterologous coding sequence which is an insecticidal coding sequence, a nematicidal coding sequence, an anti-microbial coding sequence, an anti-fungal coding sequence, an anti-viral coding sequence, a visible marker coding sequence, a selectable marker coding sequence or any combination thereof. The expression cassettes of this disclosure can be part of an expression vector, such as a plasmid.

In some embodiments, the transcriptional cassette will include in the 5'-to-3' direction of transcription, a transcriptional and translational initiation region, a heterologous nucleotide sequence of interest, and a transcriptional and translational termination region functional in plant cells. The termination region may be native with the transcriptional initiation region comprising one of the disclosed promoters, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. 1989) Nucleic Acids Res. 17:7891-7903; Joshi et al. (1987) Nucleic Acid Res. 15:9627-9639.

The expression cassettes can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene product, and can be specifically modified so as to increase translation of the mRNA.

An expression cassette including a disclosed promoter sequence operably linked to a heterologous nucleotide sequence may also contain at least one additional nucleotide sequence to be cotransformed into the organism. Alternatively, the additional sequence(s) can be provided on another expression cassette.

Where appropriate, the heterologous nucleotide sequence whose expression is to be under the control of the promoter sequence and any additional nucleotide sequence(s) may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al (1989) Nucleic Acids Res. 17:477-498.

Additional sequence modifications are known to enhance expression in a cellular host. These include elimination of sequences encoding spurious polyadenylation signals, exon-intron splice site signals, transposon-like repeats, and other such well-characterized sequences that may be deleterious to expression. The G-C content of the heterologous nucleotide sequence may be adjusted to levels average for a given cellular host, as calculated by reference to known genes expressed in the host cell. In some embodiments, sequences encoding a polypeptide is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Nat. Acad. Sci. USA 86:6126-6130); potyvirus leaders, for example, TEV leader (Tobacco Etch Virus) (Allison et al. (1986)); MDMV leader (Maize Dwarf Mosaic Virus) (Virology 154:9-20); human immunoglobulin heavy-chain binding protein (BiP) (Macejak and Sarnow (1991) Nature 353:90-94); untranslated leader from the coat protein mRNA of alfalfa mosaic virus (AMV RNA 4) (Jobling and Gehrke (1987) Nature 325:622-625); tobacco mosaic virus leader (TMV) (Gallie et al. (1989) Molecular Biology of RNA, pages 237-256); and maize chlorotic mottle virus leader (MCMV) (Lommel et al. (1991) Virology 81:382-385). See also Della-Cioppa et al. (1987) Plant Physiology 84:965-968. Other methods known to enhance translation and/or mRNA stability can also be utilized, for example, introns, and the like.

In those instances where it is desirable to have the expressed product of the heterologous nucleotide sequence directed to a particular organelle, such as the chloroplast or mitochondrion, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments may be manipulated by methods known in the art so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

The disclosed promoters may be used to drive the expression of reporter or selectable markers. Examples of suitable genes expressing reporters known in the art can be found in, for example, Jefferson et al. (1991) in Plant Molecular Biology Manual, ed. Gelvin et al. (Kluwer Academic Publishers), pp. 1-33; DeWet et al. (1987) Mol. Cell. Biol. 7:725-737; Goff et al. (1990) EMBO J. 9:2517-2522; and Kain et al (1995) BioTechniques 19:650-655; and Chiu et al. (1996) Current Biology 6:325-330. Selectable markers for selection of transformed cells or tissues can include nucleic acid sequences that when expressed confer antibiotic resistance or resistance to herbicides. Examples of suitable selectable markers include, but are not limited to, nucleic acid sequences encoding resistance to chloramphenicol (Herrera Estrella et al. (1983) EMBO J. 2:987-992); methotrexate (Herrera Estrella et al. (1983) Nature 303:209-213; Meijer et al. (1991) Plant Mol. Biol. 16:807-820); hygromycin (Waldron et al (1985) Plant Mol. Biol. 5:103-108; Zhijian et al. (1995) Plant Science 108:219-227); streptomycin (Jones et al (1987) Mol. Gen. Genet. 210:86-91); spectinomycin (Bretagne-Sagnard et al. (1996) Transgenic Res. 5:131-137); bleomycin (Hille et al. (1990) Plant Mol. Biol. 7:171-176); sulfonamide (Guerineau et al (1990) Plant Mol. Biol. 15:127-136); bromoxynil (Stalker et al. (1988) Science 242:419-423); glyphosate (Shaw et al. (1986) Science 233:478-481); phosphinothricin (DeBlock et al (1987) EMBO J. 6:2513-2518). In specific examples, the nematicidal coding sequence comprises a nucleic acid sequence encoding salicylic acid carboxylmethyltransferase (SAMT), methylsalicyalte esterase (SABP2), *Pseudomonas syringae* avr, protease inhibitors (PI) lectins and endotoxins of *Bacillus thuringiensis* disease resistance protein-like MsR1, Kunitz inhibitor ST1-like (KTI), disease resistance protein KR3, polygalacturonase inhibiting protein (PGIP).

Other genes that could serve utility in the recovery of transgenic events but might not be required in the final product would include, but are not limited to, such examples as GUS (b-glucoronidase; Jefferson (1987) Plant Mol. Biol. Rep. 5:387), GFP (green florescence protein; Chalfie et al. (1994) Science 263:802), luciferase (Riggs et al. (1987) Nucleic Acids Res. 15(19), 8115 and Luehrsen et al. (1992) Methods Enzymol. 216:397-414), and the maize genes encoding for anthocyanin production (Ludwig et al. (1990) Science 247:449).

C. Transgenics

The nucleic acid molecules of the embodiments are useful in methods directed to transiently or stably expressing a nucleotide sequence in a plant. This may be accomplished by transforming a plant cell of interest with a DNA construct comprising a promoter identified herein, operably linked to a heterologous nucleotide sequence. The methods are also directed to inducibly expressing a nucleotide sequence in a plant. Those methods comprise transforming a plant cell with a DNA construct comprising a promoter identified herein that initiates transcription in a plant cell (e.g., in an inducible manner), operably linked to a heterologous nucleotide sequence, and optionally subjecting the plant to the required stimulus to induce expression.

The expression cassette including a disclosed promoter operably linked to a heterologous nucleotide sequence of interest can be used to transform any plant, for example as a vector, such as a plasmid. In this manner, genetically modified plants, plant cells, plant tissue, seed, and the like can be obtained. Transformation protocols as well as protocols for introducing nucleotide sequences into plants may vary depending on the type of plant or plant cell, e.g., monocot or dicot, targeted for transformation. Suitable methods of introducing nucleotide sequences into plant cells and subsequent insertion into the plant genome include microinjection (Crossway et al. (1986) Biotechniques 4:320-334), electroporation (Riggs et al (1986) Proc. Natl. Acad. Sci. USA 53:5602-5606, Agrobacterium-tnediated transformation (Townsend et al, U.S. Pat. No. 5,563,055), direct gene transfer (Paszkowski et al (1984) EMBO J. 3:2717-2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology (5:923-926). Also see Weissinger et al. (1988) Ann. Rev. Genet. 22:421-477; Sanford et al. (1987) Paniculate Science and Technology 5:27-37 (onion); Christou et al. (1988) Plant Physiol 57:671-674 (soybean); McCabe et al. (1988) Bio/Technology (5:923-926 (soybean); Finer and McMullen (1991) In Vitro Cell Dev. Biol. 27P:175-182 (soybean); Singh et al. (1998) Theor. Appl Genet. 95:319-324 (soybean); Datta et al (1990) Biotechnology 5:736-740 (rice); Klein et al. (1988) Proc. Natl. Acad. Sci. USA 55:4305-4309 (maize); Klein et al. (1988) Biotechnology (5:559-563 (maize); Tomes, U.S. Pat. No. 5,240,855; Buising et al, U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol 97:440-444 (maize); Fromm et al. (1990) Biotechnology 5:833-839 (maize); Hooykaas-Van Slogteren et al. (1984) Nature (London) 377:763-764; Bytebier et al. (1987) Proc. Natl. Acad. Sci. USA 54:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9:415-418 and Kaeppler et al. (1992) Theor. Appl. Genet. 54:560-566 (whisker-mediated transformation); D'Halluin et al. (1992) Plant Cell 4:1495-1505 (electroporation); Li et al. (1993) Plant Cell Reports 72:250-255 and Christou and Ford (1995) Annals of Botany 75:407-413 (rice); Osjoda et al. (1996) Nature Biotechnology 74:745-750 (maize via Agrobacterium tumefaciens); all of which are herein incorporated by reference.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988). In: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of containing a desired polypeptide is cultivated using methods well known to one skilled in the art.

The promoter sequences and methods disclosed herein are useful in regulating expression of any heterologous nucleotide sequence in a host plant. Thus, the heterologous nucleotide sequence operably linked to the promoters disclosed herein may be a nucleic acid sequence of interest, such as a nucleic acid sequence of interest encoding a protein of interest or even a nucleic acid of interest (e.g., RNAi). Nucleic acid sequences of interest, such as ones encoding gene products of interest, are reflective of the commercial markets and interests of those involved in the development of the crop. Crops and markets of interest change, and as developing nations open up world markets, new crops and technologies will emerge also. In addition, as the understanding of agronomic traits and characteristics such as yield and heterosis increase, the choice of nucleic acid sequences of interest, such as ones encoding gene products of interest, for transformation will change accordingly. Examples of Nucleic acid sequences of interest, such as ones encoding gene products of interest, such as a transcribable DNA molecule, that when expressed in a particular plant tissue, cell, or cell type provides a desirable characteristic associated with plant morphology, physiology, growth, development, yield, product, nutritional profile, disease or pest resistance, and/or environmental or chemical tolerance. Nucleic acid sequences of interest, such as ones encoding gene products of interest, include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein (e.g., a nematicidal protein), or any other agent such as an antisense or dsRNA molecule targeting a particular gene for suppression. The product of a nucleic acid sequence of interest, may act within the plant in order to cause an effect upon the plant physiology or metabolism or may be act as a pesticidal agent in the diet of a pest that feeds on the plant.

In some embodiments, a disclosed promoter is incorporated into a construct such that the promoter is operably linked to a transcribable DNA molecule that is a nucleic acid sequences of interest, such as a nucleic acid sequence encoding a gene product of interest, such as agronomic interest. The expression of the nucleic acid sequence is desirable in order to confer an agronomically trait. Such agronomic traits may be, for example, but not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of interest known in the art include those for herbicide resistance (see for example U.S. Pat. Nos. 6,803,501; 6,448,476; and 6,107,549), increased yield (see for example U.S. Pat. Nos. 6,716,474; 6,663,906; 6,476,295; 6,441,277; 6,423,828; 6,399,330; 6,372,211; 6,235,971; 6,222,098; and 5,716,837), insect control (see for example U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (see for example U.S. Pat. Nos. 6,653,280; 6,573,361; 6,506,962; 6,316,407; 6,215,048; 5,516,671; 5,773,696; 6,121,436; 6,316,407; and 6,506,962), virus resistance (see for example U.S. Pat. Nos. 6,617,496; 6,608,241; 6,015,940; 6,013,864; 5,850,023; and 5,304,730), nematode resistance (see for example U.S. Pat. No. 6,228, 992, and International Patent Number PCT/US12/62759, which is hereby incorporated by reference), bacterial disease resistance (U.S. Pat. No. 5,516,671), plant growth and development (see for example U.S. Pat. Nos. 6,723,897 and 6,518, 488), starch production (see for example U.S. Pat. Nos. 6,538, 181; 6,538,179; 6,538,178; 5,750,876; 6,476,295), modified oils production (see for example U.S. Pat. Nos. 6,444,876; 6,426,447; and 6,380,462), high oil production (see for example U.S. Pat. Nos. 6,495,739; 5,608,149; 6,483,008; and 6,476,295), modified fatty acid content (see for example U.S. Pat. Nos. 6,828,475; 6,822,141; 6,770,465; 6,706,950; 6,660, 849; 6,596,538; 6,589,767; 6,537,750; 6,489,461; and 6,459, 018), high protein production (U.S. Pat. No. 6,380,466), fruit ripening (U.S. Pat. No. 5,512,466, which is hereby incorporated by reference), enhanced animal and human nutrition (see for example U.S. Pat. Nos. 6,723,837; 6,653,530; 6,5412,59; 5,985,605; and 6,171,640), biopolymers (see for example U.S. Pat. Nos. 6,228,623; and 5,958,745, and 6,946, 588), environmental stress resistance (U.S. Pat. No. 6,072, 103), pharmaceutical peptides and secretable peptides (see for example U.S. Pat. Nos. 6,812,379; 6,774,283; 6,140,075; and 6,080,560), improved processing traits (U.S. Pat. No. 6,476,295), improved digestibility (U.S. Pat. No. 6,531,648) industrial enzyme production (U.S. Pat. No. 5,543,576) hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

In some embodiments, a construct comprising a nucleic acid sequence operably linked to a disclosed promoter can be used to create pest resistance in susceptible plant phenotypes or to enhance pest resistance in resistant plant phenotypes. Accordingly, disclosed are methods directed to protecting plants against fungal pathogens, bacteria, viruses, nematodes, insects, and the like, for example by operably linking the coding region of a pest resistance gene to a disclosed promoter. Pest resistance genes may encode resistance to pests that have great yield drag such as rootworm, cutworm, European Corn Borer, nematodes (e.g., SCN) and the like. Disease resistance and insect resistance genes such as lysozymes, cecropins, maganins, or thionins for antibacterial protection, or the pathogenesis-related (PR) proteins such as glucanases and chitinases for anti-fungal protection, or *Bacillus thuringiensis* endotoxins, protease inhibitors, collagenases, lectins, and glycosidases for controlling nematodes or insects are all examples of useful genes. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) Gene 45:109); lecfms (Van Damme et al. (1994) Plant Mol. Biol. 24:825); and the like. Other genes encoding disease resistance traits include detoxification genes, such as against fumonosin (U.S. application Ser. No. 08/484,815, filed Jun. 7, 1995); avirulence (avr) and disease resistance (R) genes (Jones et al. (1994) Science 266:789; Martin et al. (1993) Science 262:1432; and Mindrinos et al. (1994) Cell 75:1089); and the like.

In representative embodiments, the disclosed promoters may be used to express disease resistance gene products in a root-preferred manner to prevent disease pathogens that typically infect plants through the roots.

In some embodiments, a nucleic acid sequence of interest is the coding region of a herbicide resistance gene. Such nucleic acid sequence of interest can be placed under the control of the inducible promotes disclosed herein, or alternatively included on a nucleic acid cassette to impart additional agronomic traits. Herbicide resistance traits may include the coding sequences for genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptll gene encodes resistance to the antibiotics kanamycin and geneticin, and the ALS-gene mutants encode resistance to the herbicide chlorsulfuron. Glyphosate resistance is imparted by mutant 5-enol pyruvylshikimate-3-phosphate synthase (EPSPS) and aroA genes. See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes.

See also U.S. Pat. Nos. 6,248,876; 6,040,497; 5,804,425; 5,633,435; 5,145,783; 4,971,908; 5,312,910; 5,188,642; 5,866,775; 6,225,114; 6,130,366; 5,310,667; 4,535,060; 4,769,061; 5,633,448; 5,510,471; RE 36,449; RE 37,287; and 5,491,288; and international publications WO 97/04103; WO 97/04114; WO 00/66746; WO 01/66704; WO 00/66747 and WO 00/66748, which are incorporated herein by reference for this purpose. Glyphosate resistance is also imparted to plants that express a glyphosate oxido-reductase enzyme as described more fully in U.S. Pat. Nos. 5,776,760 and 5,463, 175. In addition glyphosate resistance can be imparted to plants by the over-expression of glyphosate N-acetyltransferase. See, for example, U.S. patent application Ser. Nos. 10/004,357; and 10/427,692.

Sterility can also be encoded in a nucleic acid construct and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Commercial traits can also be encoded on nucleic acid constructs that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) J. Bacteriol. 170:5837-5847) facilitate expression of polyhyroxyalkanoates (PHAs).

Examples of other applicable expressible sequence and their associated phenotype include gene coding regions that encode a viral coat protein and/or RNA, or that confer viral resistance; that confer fungal resistance; that confer insect resistance; genes that confer nematode resistance; that promote yield improvement; and that provide for resistance to stress, such as dehydration resulting from heat and salinity, toxic metal or trace elements, or the like.

A nucleic acid sequence of interest can effect the above mentioned plant characteristic or phenotype by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. The heterologous nucleotide sequence operably linked to a disclosed promoter and its related biologically active fragments or variants disclosed herein may be an antisense sequence for a targeted gene. The terminology "antisense DNA nucleotide sequence" is intended to mean a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize to and interfere with expression of the corresponding mRNA. In this manner, antisense constructions having 70%, 80%, 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the promoter sequences disclosed herein may be operably linked to antisense DNA sequences to reduce or inhibit expression of a native protein in the plant.

"RNAi" refers to a series of related techniques to reduce the expression of genes (See for example U.S. Pat. No. 6,506, 559). Older techniques referred to by other names are now thought to rely on the same mechanism, but are given different names in the literature. These include "antisense inhibition," the production of antisense RNA transcripts capable of suppressing the expression of the target protein, and "cosuppression" or "sense-suppression," which refer to the production of sense RNA transcripts capable of suppressing the expression of identical or substantially similar foreign or endogenous genes (U.S. Pat. No. 5,231,020, incorporated herein by reference). Such techniques rely on the use of constructs resulting in the accumulation of double stranded RNA with one strand complementary to the target gene to be silenced. The promoter sequence of the embodiments, and its related biologically active fragments or variants disclosed herein, may be used to drive expression of constructs that will result in RNA interference including dsRNA, microRNAs and siRNAs.

Methods are known in the art for constructing and introducing constructs into a cell in such a manner that the transcribable DNA molecule is transcribed into a molecule that is capable of causing gene suppression. For example, posttranscriptional gene suppression using a construct with an antisense oriented transcribable DNA molecule to regulate gene expression in plant cells is disclosed in U.S. Pat. Nos. 5,107, 065 and 5,759,829, and posttranscriptional gene suppression using a construct with a sense-oriented transcribable DNA molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US2007025094). Plant pests include, but are not limited to arthropod pests, nematode pests, and fungal or microbial pests. Exemplary transcribable DNA molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

The promoter sequences and active variant thereof disclosed herein may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica), finger millet (Eleusine coracana)), sunflower (Helianthus annuus), safflower (Carthamus tinctorius), wheat (Triticum aestivum), soybean (Glycine max), tobacco (Nicotiana tabacum), potato (Solanum tuberosum), peanuts (Arachis hypogaea), cotton (Gossypium barbadense, Gossypium hirsutum), sweet potato (Ipomoea batatus), cassava (Manihot esculenta), coffee (Coffea spp.), coconut (Cocos nucifera), pineapple (Ananas comosus), citrus trees (Citrus spp.), cocoa (Theobroma cacao), tea (Camellia sinensis), banana (Musa spp.), avocado (Persea americana), fig (Ficus casica), guava (Psidium guajava), mango (Mangifera indica), olive (Olea europaea), papaya (Carica papaya), cashew (Anacardium occidentale), macadamia (Macadamia integrifolia), almond (Prunus amygdalus), sugar beets (Beta vulgaris), sugarcane (Saccharum spp.), oats, barley, vegetables, ornamentals, and conifers.

Vegetables include tomatoes (Lycopersicon esculentum), lettuce (e.g., Lactuca sativa), green beans (Phaseolus vulgaris), lima beans (Phaseolus limensis), peas (Lathyrus spp.), and members of the genus Cucumis such as cucumber (C. sativus), cantaloupe (C. cantalupensis), and musk melon (C. melo). Ornamentals include azalea (Rhododendron spp.), hydrangea (Macrophylla hydrangea), hibiscus (Hibiscus rosasanensis), roses (Rosa spp.), tulips (Tulipa spp.), daffodils (Narcissus spp.), petunias (Petunia hybrida), carnation (Dianthus caryophyllus), poinsettia (Euphorbia pulcherrima), and chrysanthemum.

Conifers that may be employed in practicing the present invention include, for example, pines such as loblolly pine (Pinus taeda), slash pine (Pinus elliotii), ponderosa pine (Pinus ponderosa), lodgepole pine (Pinus contorta), and Monterey pine (Pinus radiata); Douglas-fir (Pseudotsuga menziesii); Western hemlock (Tsuga canadensis); Sitka spruce (Picea glauca); redwood (Sequoia sempervirens); true firs such as silver fir (Abies amabilis) and balsam fir (Abies balsamea); and cedars such as Western red cedar (Thuja plicata) and Alaska yellow-cedar (Chamaecyparis nootkatensis), and Poplar and Eucalyptus. In specific embodiments, plants of the present invention are crop plants (for example, corn, alfalfa, sunflower, Brassica, soybean, cotton, safflower, peanut, sorghum, wheat, millet, tobacco, etc.). In other embodiments, corn and soybean plants are optimal, and in yet other embodiments soybean plants are optimal. Other plants of interest include grain plants that provide seeds of interest, oilseed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

In some embodiments, the polynucleotides comprising disclosed promoter operably linked to the polynucleotide encoding the polypeptide of interest are engineered into a molecular stack. Thus, the various plants, plant cells and seeds disclosed herein can further comprise one or more traits of interest, and in more specific embodiments, the plant, plant part or plant cell is stacked with any combination of polynucleotide sequences of interest in order to create plants with a desired combination of traits. As used herein, the term "stacked" includes having the multiple traits present in the same plant.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The embodiments provide compositions for screening compounds that modulate expression within plants. The vectors, cells, and plants can be used for screening candidate molecules for agonists and antagonists of the disclosed promoters. For example, a reporter can be operably linked to a disclosed promoter and expressed as a transgene in a plant. Compounds to be tested are added and reporter expression is measured to determine the effect on promoter activity. In addition, such reporters can be used to detect a pest infestation, such as a nematode infestation.

The following examples are offered by way of illustration and not by way of limitation.

EXAMPLES

Example 1

Design of Very Short and Strong Inducible Promoters Derived from Soybeanomics Data The disclosed promoters were designed using bioinformatics analysis and are inducible by soybean cyst nematode (SCN), *Heterodera glycines*, and comprise, consist essentially of, or consist of tetramerized repeats of between 6 and 20 bases (4×) located 5' adjacent to a minimal CaMV 35S promoter. In the embodiments described below, they avoid the creation of open reading frames prior to the gene of interest ATG.

SCN is an obligate sedentary endoparasite and the most important pathogen in soybean. It causes ~1 billion annually in yield losses in USA. The infection causes chlorosis, necrosis, dwarf plants with stunted shoots/roots and yellowing leaves, which are common symptoms of stress, nutrition deficiency or plant diseases. Microarray experiments detected a total of 675 genes whose expression was significantly increased during the susceptible interaction between soybean and soybean cyst nematode. A total of 49 common genes were discovered whose expression was significantly induced in this dataset and in at least one of the other 5 published microarray datasets which also studied the compatible interaction between soybean and SCNS. Using a bioinformatics analysis candidate DNA sequence motifs were determined that could logically control gene expression by SCN infection. This bioinformatics analysis used a unique combination of algorithms.

Thereafter, biological functional analysis was performed with the detected motif regions including the surrounding nucleotides as well as motifs alone in transgenic soybean hairy roots generated via *Agrobacterium rhizogenes*-mediated genetic transformation. The inducibility of each motif region or motif itself was evaluated by co-localization of the gain-of-function of an orange fluorescent protein (OFP) reporter gene and the presence of SCN in transgenic hairy roots. To clone each detected motif region or motif, primers containing XbaI and SpeI restriction sites at either end were designed to synthesize each motif region or motif. The synthesized dimers were digested with XbaI and SpeI restriction enzymes, and inserted to 5' end of OFP reporter gene (ppor RFP from *Porites porites*) in pZP222 vector which contains $^{35}$S::mGFP5-ER fusion used as an internal control (see FIG. 1). The construction of the plasmids was confirmed by sequencing. Then, the constructs were transformed into *Agrobacterium rhizogenes* strain K599, which were used to produce transgenic hairy roots in susceptible soybean line TN02-275. The reporter gene mGFP5-ER driven by $^{35}$S was used to indicate the transgenic hairy roots while the reporter gene ppor RFP was used to study the inducibility of each promoter by SCN.

Figure 2:
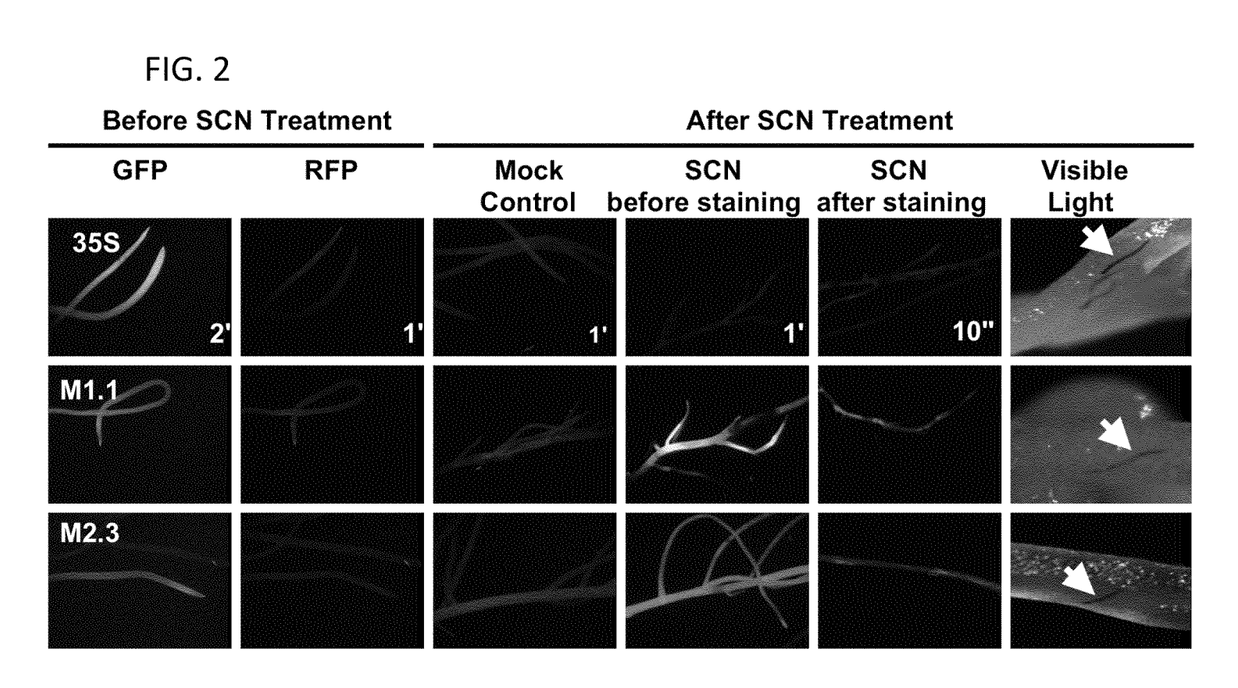
FIG. 2 is a digital image showing the inducibility of the 2 motif regions by SCN infection 3 days post infection (dpi).

Time-course analysis of ppor RFP expression was conducted to study the inducibility of each promoter by SCN at time points 3, 10, 17, 24 and 31 days post infection (dpi), using the co-localization of gain-of-function of ppor RFP reporter and the presence of SCN in hairy root assays. Expression of ppor RFP as visualized with an epifluorescent microscope (Olympus stereo microscope model SZX12, Olympus America, Center Valley, Pa., USA) and QCapture 2.56 imaging software. A tdTomato filter set (535/30 nm excitation and 600/50 nm band pass emission) was used for visualization of expression of ppor RFP. Two motifs were identified which are highly inducible by SCN infection at 3 dpi (FIG. 2; Table 1) and that are less inducible by SA treatment (Table 2) but not inducible by wounding or JA treatment. Promoter 2.3 is induced to a much lower degree by ethephon treatment.

TABLE 1

Time-course analysis of the inducibility of the two motifs by SCN infection.

| Motif # | Nucleotide Sequence (5' to 3') | Length (bp) | Time-Course Analysis of Inducibility (dpi) | | | | | |
|---|---|---|---|---|---|---|---|---|
| | | | 0 | 3 | 10 | 17 | 24 | 31 |
| 1.1 | TAAAATAAAG TTCTTTAATT (SEQ ID NO: 1) | 20 | − | +++ | +++ | ++ | − | − |
| 2.3 | ATATAATTAA GT (SEQ ID NO: 2) | 12 | − | +++ | ++ | ++ | − | − |

TABLE 2

Inducibility by non-SCN effectors. Wounding was by physical disruption by scalpel. Salicylic acid (SA), ethylene (ethephon) ERE, and jasmonic acid (JA) treatments were performed according to the methods in Liu et al. (2011).

| Motif # | Nucleotide Sequence (5' to 3') | Length (bp) | Inducibility by Effectors | | | |
|---|---|---|---|---|---|---|
| | | | Wounding | SA | ERE | JA |
| 1.1 | TAAAATAAAGTT CTTTAATT (SEQ ID NO: 1) | 20 | − | + | − | − |

TABLE 2-continued

Inducibility by non-SCN effectors. Wounding was by physical disruption by scalpel. Salicylic acid (SA), ethylene (ethephon) ERE, and jasmonic acid (JA) treatments were performed according to the methods in Liu et al. (2011).

| Motif # | Nucleotide Sequence (5' to 3') | Length (bp) | Inducibility by Effectors | | | |
|---|---|---|---|---|---|---|
| | | | Wounding | SA | ERE | JA |
| 2.3 | ATATAATTAAGT (SEQ ID NO: 2) | 12 | − | + | + | − |

Materials and Methods
Bioinformatics Analyses for De Novo SCN-Induciblee Motif Discovery Using the Affymetrix Soybean GeneChip assay, 675 genes were detected whose expression was significantly induced in the soybean genome during a susceptible soybean-SCN interaction. These induced genes were compared with other microarray datasets studying the susceptible soybean-SCN interaction, and 49 common genes were identified which overlapped between at least one of the other 5 studies. Eighteen out of 49 candidate genes were selected for de novo SCN-inducible motif discovery. Based on the sequences available through affymetrix on the world wide web, (see affymetrix.com/site/login/login.affx) and GENBANK®, the probe IDs of these 18 candidate genes were used to obtain the nucleotide sequences which were then used to design probes for microarray hybridization. Using the Phytozome website (see, phytozome.net/search.php?show=blast&blastdb=soybean as available on the world wide web), the sequences of 1-kb-long promoter regions of the 18 candidate genes were obtained for de novo motif discovery.

Plasmid Construction

A SpeI site was inserted into the region between SacI and NotI sites in plasmid pZP4×PR1RFP (see Liu et al., BMC Biotechnology, 11:108, 2011, which is incorporated herein by reference in its entirety) by PCR using primers pZP4× PR1-SacI-SpeI-F and pZP-BamHI—R, followed by double restriction enzyme digestion with SacI and BamHI. The new construct was named as pZPSpeI4×PR1-4635S RFP. Using plasmid pBIN-m-GFP5-ER as template, the fragment of CaMV 35 promoter, m-GFP5-ER and NosT were fused together by 5 rounds of PCR amplification with primers (1) p35S-HindIII-F and p35S-GFP-R, (2) p35S-GFP-F and pGFP-Nos-R, (3) pGFP-Nos-F and pNos-HindIII-R, (4) p35S-GFP-F and pNos-HindIII-R, and (5) p35S-HindIII-F and pNos-HindIII-R, respectively. At the same time, the restriction sites of BamHI and SacI were removed from that fragment. This PCR fragment was purified and inserted into the HindIII site of plasmid pZPSpeI4×PR1-4635S RFP to make a construct pZPSpeI4×PR1-4635S RFP-35S GFP.

Figure 1A:
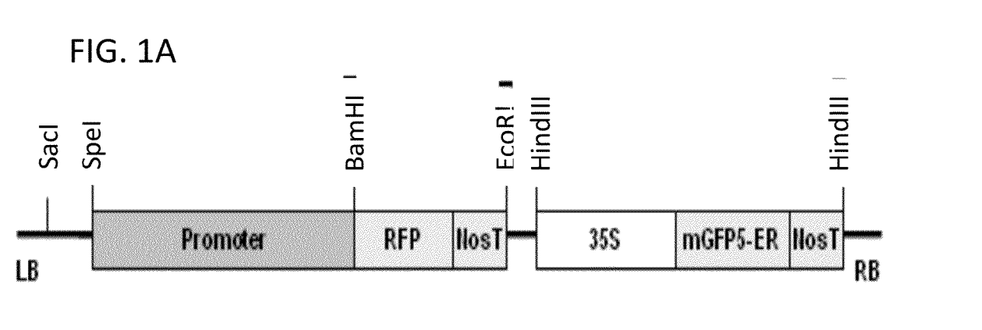
FIGS. 1A and 1B are schematic diagrams of plasmids pZPSpeI Promoter RFP-35SGFP (A) and pZPSpeI 4×M RFP-35SGFP (B) showing the characterized promoter motifs 1.1 and 2.3 that were introduced into the functional cassette at "motif" locations for functional analysis in hairy roots from soybean.
Figure 1B:
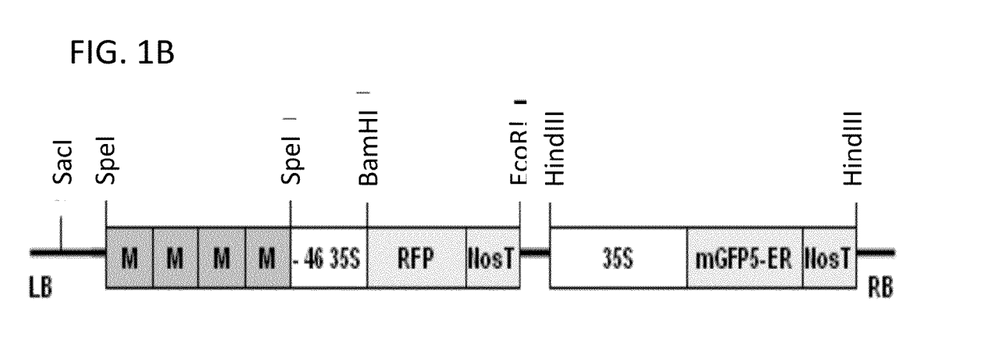

The seven 1-kb-long soybean promoter regions were PCR amplified from the genomic DNA of soybean line TN02-275 (Mazarei et al., Theor. Appl. Genet. 123:1193-1206, 2011, which is incorporated herein by reference in its entirety), and used to replace 4×PR1-46 35S fragment in plasmid pZPSpeI4×PR1-4635S RFP35S GFP with the help of restriction enzymes SpeI and BamHI (FIG. 1A). The primer dimer of each tetramerized motif region as well as motif alone was synthesized via fusion of two primers, which were reverse complementary to each other. Then, each primer dimer was digested with XbaI+SpeI and inserted into SpeI-digested pZPSpeI4×PR1-4635S RFP-35S GFP (FIG. 1B).

Plant Materials

Soybean line TN02-275, which is susceptible to the SCN race 2 (HG type 1.2.5.7; Mazarei et al. 2011), was used in this study. Sterile soybean seeds were germinated in sealed sterile petri dishes for three days. Then seedlings were transferred into sterilized vermiculite for another 4 days in a growth chamber at 25° C. under fluorescent white light in a 16:8 h light/dark cycle. Seedlings were watered using sterile B&D solution containing 1 mM $CaCl_2$, 0.5 mM $KH_2PO_4$, 10 µM Fe-citrate, 0.25 mM $MgSO_4$, 0.25 mM $K_2SO_4$, 1 µM $MnSO_4$, 2 µM $H_3BO_4$, 0.5 µM $ZnSO_4$, 2 µM $CuSO_4$, 0.1 µM $CoSO_4$, 0.1 µM $Na_2MoO_4$, and 1 mM $KNO_3$.

Generation of Transgenic Soybean Hairy Roots

Transgenic soybean hairy roots were generated as described (Cho et al., Planta. 2000 January;210(2):195-204; Kereszt et al., Nat. Protoc. 2007; 2(4): 948-52) with modifications. *Agrobacterium rhizogenes* strain K599 was transformed with each individual construct by electroporation. *A. rhizogenes* containing individual constructs was grown on yeast extract peptone [(YEP), 10 g/L yeast extract, 10 g/L peptone, 5 g/L NaCl, 15 g/L agar] solid medium supplemented with spectinomycin (200 mg/L), and streptinomycin (50 mg/L) at 28° C. for 2 days. One single colony was inoculated in two of 250 ml YEP liquid medium and was spread onto two YEP solid medium supplemented with the above-mentioned antibiotics, and grown for ~2 days at 28° C. The cultured bacteria lawn was collected and suspended in 1 ml of sterile distilled water. Bacterial suspension was injected into one-week-old soybean cotyledonary nodes and upper hypocotyls with unfolded cotyledons for three times with a 3-ml needle syringe. After injection, soybean seedlings were covered with transparent plastic covers that were sprayed with water and maintained in a growth chamber for 1 week. Then, the plastic covers were removed and the *A. rhizogenes* wounding sites were covered by sterile vermiculite. About 20 biological replicates (e.g. 20 plants) were used for each construct.

Three weeks later, the hairy roots grew to approximately 10 cm in length. Transgenic soybean hairy roots were screened for GFP expression with an epifluorescent microscope (Olympus stereo microscope model SZX12, Olympus America, Center Valley, Pa., USA) using a GFP filter set and QCapture 2.56 imaging software. The tap roots and non-transgenic roots were excised.

Nematode Source

A SCN race 2 (HG type 1.2.5.7), which was originally collected from soybean welds in Beaufort County, N.C., USA, was cultured in the greenhouse under controlled conditions of temperature and light, and maintained on the roots of cv. Pickett-71 (see Hartwig et al., Crop Sci 11:603, 1971) before used for inoculum preparation (see Arelli et al., Crop Sci 40:824-826, 2000).

Nemotode Infection and Tissue Harvesting

Transgenic soybean hairy roots harboring the same construct were loaded horizontally in a 13×9×2 cm sterilized inoculating tray containing a thin layer of mixture of sterile sand and top soil (1:1). About 10 ml of inoculum, which contained about 66,000 SCN eggs, was added to each inoculating tray. SCN eggs were allowed to hatch and infect soybean roots for 7 days under humid conditions. Then all the roots were taken out and washed to remove extra SCN eggs and juvenile nematodes that had not penetrated the root tissues. The infected chimeras were grown in containers with sterile vermiculite in a growth chamber. Infected transgenic hairy root tissues were cleared by 20% (v/v) bleach for about 4-7 min, and then stained by acid fuschin for detection of nematodes according to Byrd et al. (Journal of Nematology 14:142-143, 1983) at time points of 3, 10, 17, 24 and 31 dpi.

Abiotic Treatments

Wounding was performed by repeatedly piercing the 4-week-old transgenic soybean hairy roots containing each construct with a needle. The wounded plants were incubated in B&D solution for 24 hours. Unwounded transgenic soybean hairy roots were incubated in B&D solution for 24 hours as mock control.

For chemical treatments, 4-week-old transgenic soybean hairy roots containing each construct were incubated in the B&D solution containing 4 mM salicylic acid (SA), 4 mg/ml ethephon (an ethylene releasing chemical), or 100 µM methyl jasmonate (MeJA) (all from Sigma, St. Louis, Mo., USA) for 3 days. For mock control treatments, transgenic hairy roots were incubated in the B&D solution for 3 days.

Determination of Gain-of-Function of pporRFP Expression

Expression of the red fluorescence reporter gene, ppor RFP, was visualized with an epifluorescent microscope (Olympus stereo microscope model SZX12, Olympus America, Center Valley, Pa., USA) and QCapture 2.56 imaging software. A tdTomato filter set (535/30 nm excitation and 600/50 nm band pass emission) were used for visualization of expression of ppor RFP. Time-course analyses of the expression of ppor RFP reporter were conducted at time points 3, 10, 17, 24, and 31 days post inoculation (dpi).

Example 2

Determination of Promoter Activity by Transient Expression

To determine if the activity of the disclosed promoters is tissue specific, promoter activity is tested on the leaves of non-transgenic soybean by agroinfiltration. In some trials, the constructs pZP-4635S OFP-35S GFP (as negative control), pZP4×M1.10FP-35S GFP and pZP4×M2.30FP-35S GFP are tested for on the leaves of non-transgenic soybean by agroinfiltration.

The constructs are transferred into *Agrobacterium tumefaciens* strain EHA105 (see for example using a protocol similar to that disclosed in An et al., Binary vector. In: Gelvin S B, Schilproot R A (eds), Plant molecular biology manual. Kluwar Academic Publishers, Dordrecht, pp A3 1-19 (1988)). Preparation of *Agrobacterium* cultures is carried out using conventional methods known in the art. In-planta transient expression system is established using soybean seedlings. Agroinfiltration is tested on seedlings at various stages of development to determine which worked best for agroinfiltration. Plant tissue is harvested several days post infiltration for subsequent analysis. Promoter activity is determined based on the expression of the fluorescent reporter gene.

Example 3

Generation of Stable Transgenic Soybean pZP4×M1.10FP-35S GFP, pZP4×M2.30FP-35S GFP and pZP-4635S OFP-35S GFP are transformed into soybean. Soybean seeds are utilized in the *Agrobacterium*-mediated transformation experiments. Tissue-specific expression of each construct is analyzed in the stable transgenic soybean.

Transgenic soybeans are also inoculated with SCN eggs. The eggs are allowed to hatch and infect soybean roots for 3 days under humid conditions. Then all the roots were taken out and washed to remove extra SCN eggs and juvenile nematodes that had not penetrated the root tissues. The infected chimeras were grown in cone-tainers with sterile vermiculite in a growth chamber. Infected transgenic hairy root tissues were cleared by 20% (v/v) bleach for about 4-7 min, and then stained by acid fuschin for detection of nematodes according to Byrd et al. (Journal of Nematology 14:142-143, 1983) at time points of 3, 10, 17, 24 and 31 dpi. A set of uninfested plants is kept as a control group.

pZP4×M1.10FP-35S GFP or pZP4×M2.30FP-35S GFP, and pZP-4635S OFP-35S GFP are transformed into *Arabidopsis thatliana* Columbia. Seeds *A. thaliana* Columbia were used for *Agrobacteria*-mediated transformation. Tissue-specific expression of each construct is analyzed in the stable transgenic *Arabidopsis* plants. The stable transgenic plants are also challenged with nematode eggs, such as root-knot nematode (*M. incognita*) eggs. A set of uninfested plates is kept as a control group. At several timepoints, roots are harvested from both infested and noninfested plants at time points of 3, 10, 17, 24 and 31 dpi.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, chemical moieties, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims.

tion, an environmental condition associated with pathogen expression or a combination thereof.

3. The isolated nucleic acid molecule of claim 2, wherein the pathogen is a nematode.

4. The isolated nucleic acid molecule of claim 3, wherein the nematode is a soybean cyst nematode.

5. An expression cassette comprising the isolated nucleic acid molecule of claim 1 operably linked to a heterologous coding sequence.

6. The expression cassette of claim 5 wherein the heterologous coding sequence comprises an insecticidal coding sequence, a nematicidal coding sequence, an anti-microbial coding sequence, an anti-fungal coding sequence, an anti-viral coding sequence, a visible marker coding sequence, a selectable marker coding sequence or any combination thereof.

7. The expression cassette of claim 6, wherein the nematicidal coding sequence comprises a nucleic acid sequence encoding salicylic acid carboxyl methyltransferase (SAMT), methylsalicyalte esterase (SABP2), *Pseudomonas syringae* avr, a protease inhibitor (PI) a lectin, an endotoxin of *Bacillus thuringiensis* disease resistance protein-like MsR1, a Kunitz inhibitor ST1-like (KTI), a disease resistance protein KR3, a polygalacturonase inhibiting protein (PGIP) or a combination thereof.

8. An expression vector comprising the expression cassette of claim 5.

9. The expression vector of claim 8, wherein the vector is a plasmid.

10. A transgenic plant or part thereof, comprising the isolated nucleic acid molecule of claim 1.

We claim:

1. An isolated nucleic acid molecule that directs induced expression in a plant cell, wherein the nucleic acid molecule comprises a promoter comprising four consecutive repeats of the nucleic acid sequence set forth as SEQ ID NO: 1 or SEQ ID NO: 2 and a minimal promoter.

2. The isolated nucleic acid molecule of claim 1, wherein the promoter directs expression in a plant cell of an operably linked nucleic acid sequence, wherein the expression is induced by a pathogen elicitor treatment, a pathogen infec- 11. The transgenic plant or part thereof of claim 10, wherein the isolated nucleic molecule is stably incorporated into its genome.

12. The transgenic plant or part thereof of claim 10, wherein the plant is a dicot.

13. The transgenic plant or part thereof of claim 12, wherein the dicot is soybean.

14. The transgenic plant or part thereof of claim 12, wherein the dicot is a *Brassica* plant, a sunflower plant, a cotton plant, or an alfalfa plant.

15. The transgenic plant or part thereof of claim 10, wherein the plant is a monocot.

16. The transgenic plant or part thereof of claim 15, wherein with monocot is maize, wheat, rice, barley, sorghum, sugar cane or rye.

17. A seed, leaf, root or cell of the transgenic plant of claim 10, wherein the seed, leaf, root or cell comprises said isolated nucleic acid molecule.

18. A method of regulating the expression of a polynucleotide of interest, comprising:
   transforming a plant or plant cell with the polynucleotide of interest operably linked to a promoter wherein the promoter comprises the isolated nucleic acid molecule of claim 1; and
   contacting the plant or plant cell with a substance or organism that induces the promoter.

19. A commodity plant product, comprising the isolated nucleic acid of claim 1, wherein the commodity plant product is protein concentrate, protein isolate, soybean hulls, meal, flour or oil.

20. A method of producing a transgenic plant comprising:
   transforming a plant cell with a polynucleotide sequence of interest operably linked to a promoter wherein the promoter comprises the isolated nucleic acid molecule of claim 1.

* * * * *